United States Patent [19]

Nilson

[11] 4,047,642
[45] Sept. 13, 1977

[54] SPRAYING DEVICE

[76] Inventor: Billy Nils Nilson, 595 00 Mjolby, Sweden

[21] Appl. No.: 453,344

[22] Filed: Mar. 21, 1974

[30] Foreign Application Priority Data

Mar. 22, 1973 Sweden .............................. 7304094

[51] Int. Cl.² .......................................... B65D 35/28
[52] U.S. Cl. .................... 222/94; 128/187; 222/95; 222/131; 222/215; 239/327
[58] Field of Search ............... 128/187, 186, 195, 198, 128/199, 201, 205, 206, 208; 222/93, 94, 130, 131, 193, 211, 215, 187, 192, 214; 239/327, 34

[56] References Cited

U.S. PATENT DOCUMENTS

| 465,484 | 12/1891 | Magoris | 222/193 |
| 2,794,579 | 6/1957 | McKernan | 222/399 |
| 3,147,888 | 9/1964 | Mooney | 222/130 |
| 3,217,931 | 11/1965 | Farrar | 222/94 |
| 3,471,064 | 10/1969 | Micallef | 222/211 |
| 3,635,375 | 1/1972 | Gaetke | 222/94 |

Primary Examiner—Robert B. Reeves
Assistant Examiner—Joseph J. Rolla
Attorney, Agent, or Firm—Ulle C. Linton

[57] ABSTRACT

A spraying device comprises an outer compressible container and an inner compressible container. The outer container the interior of which having no communication with the surrounding atmosphere contains a preferably liquid active substance whereas the inner container initially contains air. The inner container communicates with the atmosphere via a narrow channel whereas the inner container is made permeable such that active substance may reach the inner container in small quantities. Squeezing of the outer container will thus generate a spray comprising air and active substance. The device may further have openings to enable air to be suck into the inner container after each use of the device.

1 Claim, 3 Drawing Figures

U.S. Patent     Sept. 13, 1977     4,047,642

SPRAYING DEVICE

This invention relates to a spraying device, i.e. a device intended to generate a directed spray of air containing extremely fine divided substances such a medically acting substances.

Such spraying devices are used for example by asthmatical persons, for disinfectant purposes, to perfume and the like.

The primary object of the invention is to provide a spraying device that may be manufactured to a very low cost but despite of this fulfills the requirements upon such a device, that is the ease of handling, a convenient size, a full utilization of the active substance, etc.

To accomplish these and other objects the invention has the characteristics disclosed in the claims.

Figure 1:
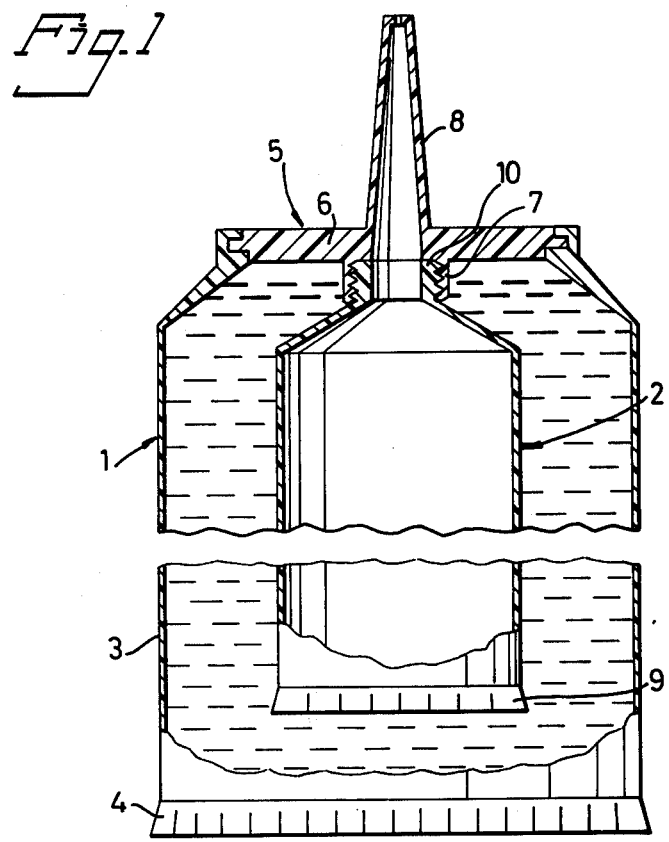
Figure 2:
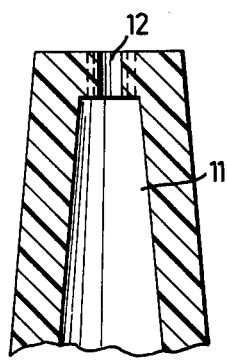
Figure 3:
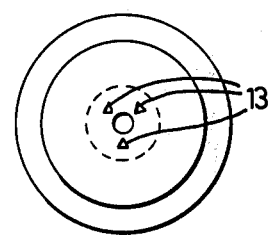

In the accompanying drawing an examplifying embodiment of the invention is shown, and FIG. 1 is a longitudinal section through a tube, manufactured according to the invention, FIG. 2 is a section on a larger scale through the opening of the tube shown in FIG. 1, and finally FIG. 3 is an end view of the tube opening according to FIG. 2.

In the embodiment of the invention illustrated in the drawing the spraying device comprises an outer tube having the general designation 1 and an inner tube with the general designation 2. In this case the outer tube is made of a metal and has a thin tube pipe 3, which in manner known per se such as by flat welding and bending, is closed at one end 4 thereof and in the other end thereof is connected to a portion generally designated 5 defining the tube opening. This tube opening portion is much stiffer, as can be seen is FIG. 1, as to its structure than the thin tube pipe 3 and comprises a plate 6, a sleeve 7 projecting from this plate in one direction thereof. The inner tube 2 is connectable to said sleeve.

A cannula 8 projects from the plate in the opposite direction. The connection between the inner tube 2 and the sleeve 7 may be accomplished as can be seen in FIG. 1 by threading of both elements, but of course it may be accomplished in every other known manner. The inner tube has similarly to the outer tube a closed end portion 9 and an opening portion 10, the opening of which communicating with the opening of the cannula 8.

In the embodiment shown, the inner tube is made from an elastically yieldable plastic material with permeable characteristics. Said inner tube initially only contains air while the outer tube is filled with the active substance, such as an aromatic oil. Due to the permeability of the inner tube the air enclosed in the inner tube will be concentrated with said active substance and due to the elastically yieldable characteristics of the inner container a pressure upon the outer compressible tube will result in a corresponding squeeze of the inner tube, whereby the air containing the active substance flows out through the opening 11, 12 of the cannula 8.

By providing the cannula with a first opening according to FIG. 2 and a weaker second opening 12 and provision of a number of small holes 13 in the merge portion between the holes 11 and 12 according to FIG. 3 re-sucking of air into the inner tube is facilitated when the pressure upon the outer tube is released.

Naturally, the outer tube similarly to the inner may be made from a plastic material having elastically yieldable characteristics but this material should, opposite to the material of the inner tube, be practically impermeable to liquid.

Furthermore, the tube pipe 3 and the tube opening may be integrally made, whereby the connection of the inner tube is accomplished by means of a special tool for the closing by 4 of the outer tube.

While the device shown and described herein in which a generally negatively considered characteristic of the plastic material, i.e. the characteristic thereof to permit the passage of small amounts of a liquid, is utilized to concentrate the air enclosed in the inner tube may be considered to be the easiest and best solution to the problem it is also possible to accomplish the addition of substance to the air in other ways. Thus, it is possible to provide a wick in the inner tube that depends into the outer tube and to provide a capillary tube that extends through the bottom of the inner tube and up into the cannula, respectively.

Also in other details the invention may be varied within the scope of the claims.

I claim:

1. Spraying device comprising an outer receptacle having a flexible wall, an inner receptacle also having a flexible wall, said inner receptacle being housed in said outer receptacle, a liquid active substance being contained in said outer receptacle, said inner receptacle initially containing only air and communicating with the atmosphere via a narrow channel, said inner receptacle wall being imperforate and of a permeable material, and the permeable nature of said inner receptacle wall being the sole means for transferring the active substance to be dispensed from said outer receptacle to said inner receptacle whereby upon squeezing said outer receptacle said liquid therein is passed into said inner receptable for dispensing with the initial air charge in said inner receptacle.

* * * * *